US012599401B2

(12) United States Patent
Ronfard et al.

(10) Patent No.: US 12,599,401 B2
(45) Date of Patent: Apr. 14, 2026

(54) METHODS AND SYSTEMS FOR PRODUCING SKIN GRAFTS

(71) Applicant: CUTISS AG, Schlieren (CH)

(72) Inventors: Vincent Ronfard, Villarzel (CH);
Claude Holenstein, Zürich (CH);
Anna-Lena Dittrich, Zumikon (CH);
Laurent Barnes, Zürich (CH); Reto Frei, Turgi (CH); Ulrich Öffinger,
Rieden AG (CH); Boris Stolz,
Pfaffhausen (CH)

(73) Assignee: Cutiss AG, Schlieren (CH)

( * ) Notice: Subject to any disclaimer, the term of this
patent is extended or adjusted under 35
U.S.C. 154(b) by 944 days.

(21) Appl. No.: 17/778,962

(22) PCT Filed: Nov. 22, 2020

(86) PCT No.: PCT/IL2020/051202
§ 371 (c)(1),
(2) Date: May 23, 2022

(87) PCT Pub. No.: WO2021/100047
PCT Pub. Date: May 27, 2021

(65) Prior Publication Data
US 2023/0000513 A1      Jan. 5, 2023

Related U.S. Application Data

(60) Provisional application No. 62/938,985, filed on Nov.
22, 2019.

(51) Int. Cl.
| | |
|---|---|
| *A61B 17/322* | (2006.01) |
| *A61L 27/38* | (2006.01) |
| *A61L 27/60* | (2006.01) |

(52) U.S. Cl.
CPC ........ *A61B 17/322* (2013.01); *A61L 27/3813*
(2013.01); *A61L 27/3886* (2013.01); *A61L
27/60* (2013.01); *A61B 2017/3225* (2013.01)

(58) Field of Classification Search
None
See application file for complete search history.

(56) References Cited

U.S. PATENT DOCUMENTS

| | | | |
|---|---|---|---|
| 8,709,081 B2 | 4/2014 | Kharazi et al. | |
| 2006/0105454 A1 | 5/2006 | Son et al. | |
| 2007/0243158 A1 | 10/2007 | Ronfard et al. | |
| 2011/0201115 A1 | 8/2011 | Pearlman et al. | |
| 2012/0308531 A1 | 12/2012 | Pinxteren et al. | |
| 2013/0295061 A1 | 11/2013 | Maslowski | |
| 2014/0315303 A1* | 10/2014 | Huang | B01L 3/502 |
| | | | 435/366 |
| 2015/0079153 A1 | 3/2015 | Quick et al. | |
| 2015/0152375 A1 | 6/2015 | Hedrick et al. | |
| 2016/0271299 A1 | 9/2016 | Galue | |
| 2017/0136148 A1* | 5/2017 | Tumey | A61L 27/3604 |
| 2017/0175063 A1 | 6/2017 | Smith et al. | |

FOREIGN PATENT DOCUMENTS

| | | |
|---|---|---|
| WO | WO-2006/005977 A1 | 1/2006 |
| WO | WO-2010/130302 A1 | 11/2010 |
| WO | WO 2010/130305 A1 | 11/2010 |
| WO | WO 2016/015754 A1 | 2/2016 |
| WO | WO 2018/122039 A1 | 7/2018 |
| WO | WO 2020/245818 A1 | 12/2020 |
| WO | WO 2021/156872 A1 | 8/2021 |

OTHER PUBLICATIONS

Böttcher-Haberzeth, S., et al. "Tissue engineering of skin," *Burns*,
vol. 36, Issue 4, Jun. 2010, pp. 450-460.
Extended European Search Report, European Patent Office Appli-
cation No. 20888866.9, dated Dec. 4, 2023, 11 pages.
Meuli, M., et al., "A Cultured Autologous Dermo-epidermal Skin
Substitute for Full-Thickness Skin Defects: A Phase I, Open,
Prospective Clinical Trial in Children," *Plastic and Reconstructive
Surgery*, Jul. 2019, vol. 144, Issue 1, pp. 188-198.
PCT International Search Report and Written Opinion, PCT Appli-
cation No. PCT/IL2020/051202, Jan. 31, 2021, 18 pages.

* cited by examiner

*Primary Examiner* — Nghi V Nguyen
(74) *Attorney, Agent, or Firm* — Fenwick & West LLP

(57) ABSTRACT
Various methods for producing skin grafts for rehabilitation
of skin defects are carried out in a closed system operated
and controlled in an automated manner. A skin biopsy may
be separated into a dermis layer and an epidermis layer prior
to formation of a skin graft. A total skin graft area produced
may be 9 times to 1000 times greater than a total skin biopsy
area that provides cells for the graft. Differences in density
between dermis and epidermis may aid in separation
between a dermis layer and an epidermis layer.

9 Claims, 11 Drawing Sheets

METHODS AND SYSTEMS FOR PRODUCING SKIN GRAFTS

FIELD OF THE INVENTION

The present invention is in the field of medical devices, tissue engineering and regenerative medicine. More particularly, the invention relates to a method and system for producing skin grafts for rehabilitation of skin defects.

BACKGROUND OF THE INVENTION

When a person suffers from severe skin defects, the affected skin area needs to be replaced to provide protection to the body. This skin replacement requires unpleasant treatments, even only for the chance of a slight improvement. Current treatment regimens often result in permanent, painful, disfiguring, and debilitating scars, which may impair mobility and growth, and often require several follow-up surgeries, intense homecare and psychosocial rehabilitation.

Damaged skin is in many cases treated by surgical means. A common treatment is based on the process of removing the damaged skin, harvesting healthy layers of skin, and transplanting them on the section of the body that had the damaged skin, which needs to be restored. Human skin is the largest organ of the Human body. It is comprised of an outer layer, which is called "epidermis", and a deeper layer called "dermis". Both epidermis and dermis layers, either combined or separately, are used in the process of skin grafting and transplanting. It is usually recommended to harvest the healthy skin layers from another part of the body of the patient for the use of skin grafting (a process that is hereinafter also referred to as "autografting"), thus preventing the risk of rejection. Typically, the harvested skin is a split-thickness skin biopsy, which only consists of the epidermis and a very small part of the dermis, so that the scarring at the harvesting location is minimized. However, grafting split-thickness skin grafts (STSGs) onto full-thickness wounds may results in scarring at the graft site due to incomplete dermis layer. In addition, if the transplantation needs to be performed on a large area of the body, it can be very harmful and sometimes not possible to harvest enough transplantable skin. In this case, the harvest site needs to heal and regenerate before more transplantable skin can be harvested, leading to a long series of surgeries which causes long hospitalization periods, high costs and distress for the patients.

It is possible to isolate and grow skin cells in a laboratory, originating from humans, and transplanting them to a patient. But such a process includes several stages that require exposing the cells to the environment. The first stage is to obtain a skin biopsy, and then the skin can be processed and cut into smaller pieces. When reaching the desired size of skin pieces, the sample undergoes a washing process (if it hasn't already been washed before cutting) and then the two main types of skin cells (i.e., keratinocytes and fibroblasts) are separated as single cell suspension or tissue explants and inserted into a culture vessel with cell culture media, suitable to allow cell growth. The medium needs to be changed along the process, in order to extract unnecessary cell products and allow the continuation of the growth process. The manual change of the medium exposes the cells to the environment, resulting in possible risks of contaminations. Other types of skin cells, such as melanocytes, endothelial cells, and other mesenchymal-derived cells can also be cultured in vitro under appropriate culture conditions and incorporated into the skin graft to be implanted to the patient.

Another disadvantage of cell growing according to common practice is the fact that many stages require human interference, which involves risks of: (1) damaging the sample due to human errors; and (2) contaminating the sample. It also requires extensive working hours, and the level of accuracy depends on the professional level of the lab technicians, which limits the scalability of amplification. Furthermore, all operations have to be performed in a certified cleanroom area of class A following Good Manufacturing Practices (GMP) guidelines, which is expensive to operate.

It is an object of the present invention to provide a method and system for producing personalized skin grafts.

It is another object of the present invention to provide a more reproducible, reliable, safer and efficient method and system for skin graft production.

Other objects and advantages of the invention will become apparent as the description proceeds.

SUMMARY OF THE INVENTION

In one aspect, the present invention provides a method for producing a skin graft, comprising:

receiving a skin biopsy sample by a cell preparation device from a biopsy kit docketed to said cell preparation device;

optionally, separating the skin biopsy into dermis layer and epidermis layer in a layer separation apparatus and transferring the dermis layer into a fibroblast isolation apparatus and the epidermis layer into a keratinocyte isolation apparatus;

isolating single cell suspension of fibroblasts and keratinocytes from the biopsy sample or from the separated dermis and epidermis layers of the biopsy sample respectively, wherein the isolation of fibroblasts is carried out in a fibroblast cell isolation apparatus and the isolation of keratinocytes is carried out in a keratinocyte cell isolation apparatus, and transferring the isolated fibroblasts and the isolated keratinocytes to a respective cell expansion device;

expanding fibroblasts and keratinocytes in their respective cell expansion device, and transferring the expanded fibroblasts and keratinocytes to their respective post-expansion processing devices;

processing the fibroblasts and keratinocytes in their respective post-expansion processing devices and transferring the processed fibroblasts and keratinocytes to a tissue formation device; and forming a skin graft comprising fibroblasts and keratinocytes in a tissue forming device;

wherein, receiving, separating, isolating, expanding, processing, and forming are subject to automatic control.

In some embodiments of the invention, the transferring of the dermis layer, epidermis, layer, isolated fibroblasts and keratinocytes, expanded fibroblasts and keratinocytes, and processed fibroblasts and keratinocytes is subject to automatic control.

In one embodiment of the invention, the method further comprises adding at least one of melanocytes, endothelial cells and skin mesenchymal-derived cells to said tissue formation device.

In another embodiment of the invention, the ratio between the size of the biopsy size and the size of the skin graft is 1:9 to 1:1000.

In another aspect, the present invention provides a system for automated skin graft production, the system comprising at least one cell preparation device, at least one cell expansion device, at least one post-expansion processing devices and least one tissue forming device.

In one embodiment, the cell preparation device comprises at least one cell isolation apparatus. In a further embodiment, the cell preparation device further comprises at least one layer separation apparatus.

In another embodiment, the system is a closed system.

In yet another embodiment, the system comprises disposables.

In a further embodiment, the system is adapted to perform sterile transfer of the biopsy, the skin layers or the cells between the apparatuses and/or devices of the system.

In yet another aspect of the invention, there is provided a method comprising:

inserting a skin biopsy into a skin graft production system; and producing a plurality of skin grafts;

wherein the ratio between the size of the biopsy and the total size of the plurality of skin grafts is 1:9 to 1:1000.

According to one embodiment, the biopsy is a split-thickness biopsy and the skin graft is a full-thickness skin graft.

DETAILED DESCRIPTION

The method and system according to the present invention, relate to an automatic or a semi-automatic process for the manufacturing of bio-engineered living skin tissue (also termed "skin graft") starting with pre-processing a skin biopsy sample and up until forming a tissue suitable for transplantation. A major advantage of the method of the invention over known autografting methods is the ability to produce a large area of skin graft to treat a large area on the patient's body starting from a small skin sample harvested from said patient. The large area of available graft tissue emanates from the combined effect of proliferating the cells isolated from the biopsy and the simultaneous production of multiple skin grafts from a single biopsy. Accordingly, while current autografting of STSGs are characterized by a ratio of 1:3 between the harvest size and the treatment size, the method of the present invention provides a ratio of about 1:1000 between the harvest size and the treatment size. This feature enables spares the patient from undergoing multiple medical procedures, thereby minimizing the damage and stress caused to the patient.

Figure 9:
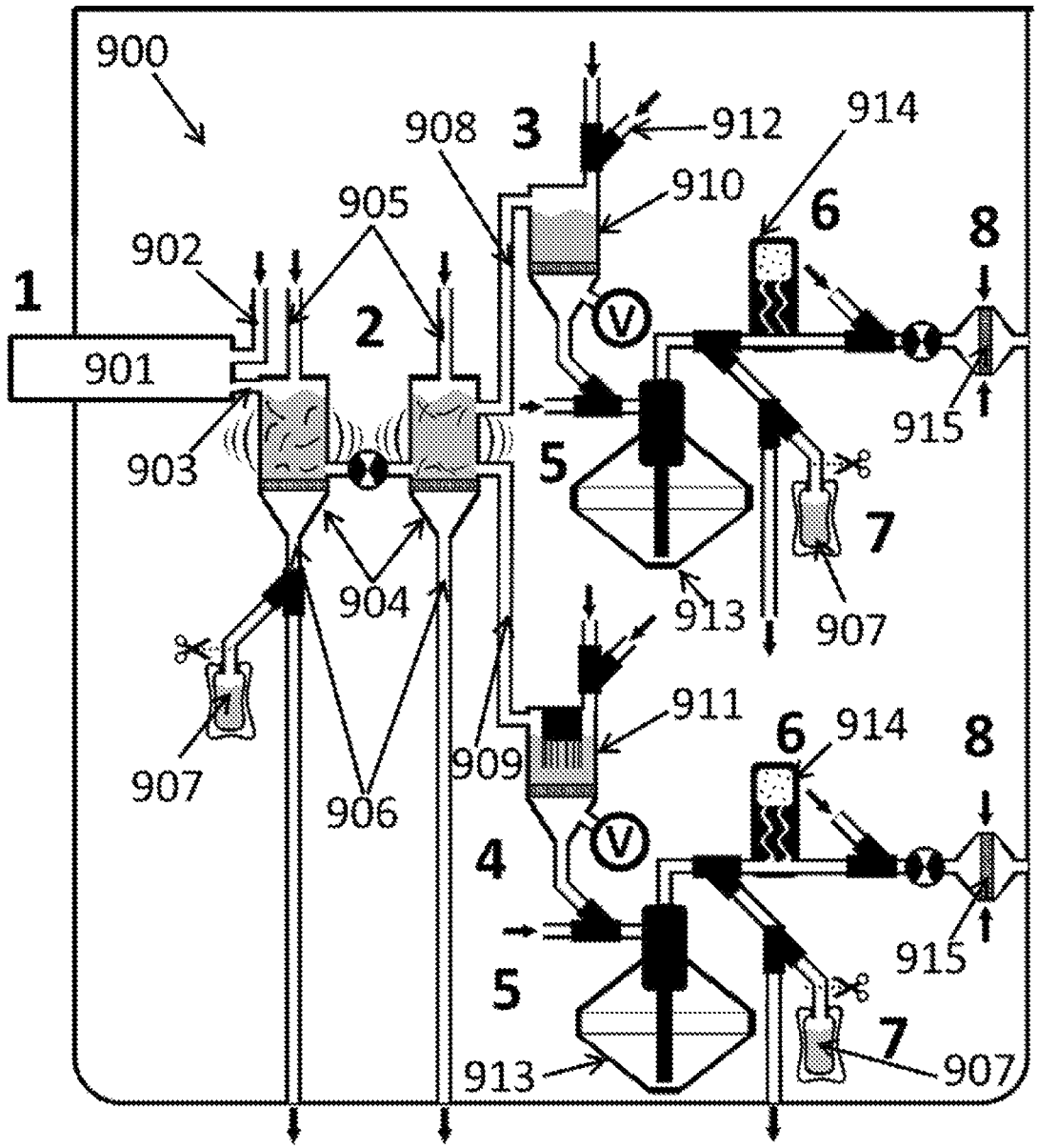
FIG. 9 is a schematic overview of separation and isolation chambers in a cell preparation device, according to one embodiment of the invention.

The method according to the present invention comprises connecting a biopsy kit to a separation chamber (as shown in FIG. 9 by component 901) or to an isolation chamber in order to transfer a biopsy sample into the said separation or isolation chamber. Thus, a skin biopsy is received by the system of the invention. The biopsy kit is suitable to secure the biopsy and hold it in place, and also provide the conditions for keeping it vital. The securing means of the biopsy inside the kit can be any type of mechanical means that do not harm the tissue and prevent its movement, such as gentle nail-shaped component, or surfaces that hold it in place by applying slight pressure. Another option of placing the tissue inside the biopsy kit is filling the kit with a fluid, suitable to come in contact with the tissue, and allowing its floatation. Furthermore, the biopsy maybe held in place by a biocompatible adhesive. During transport from the hospital, where the biopsy is harvested from the patient, to the GMP laboratory where the graft manufacturing is carried out, the biopsy needs to be submerged in a suitable transport solution containing nutrients and may also contain antimicrobial compounds, which need to be introduced in the biopsy kit. In the case of mechanical fixation, the kit can further comprise a compartment filled with a suitable solution and means for dipping the tissue inside the solution. In case of the fluid compartment, the fluid can be any type of solution that is suitable for transportation.

Another stage that can be performed inside the biopsy kit is the cutting of the tissue. In order for the enzymes to work more efficiently, the skin may be cut into smaller pieces. According to one embodiment of the invention, the cutting is performed by a laser cutter, which also enables a selective cutting of the epidermis layer. The laser beam can be focused on the skin while moving the skin layer, or alternatively, the beam can move instead of the layer. According to another embodiment of the invention, the biopsy kit comprises either counter-rotating knifes, rolling knifes, or moving blades that are operated manually or by electronic means. Integrating the cutting tools inside the biopsy kit prevents additional exposure of the cells and provides a more efficient and faster process.

The skin biopsy mainly contains two skin layers, the outermost epidermis layer mainly comprising keratinocytes and the inner dermis layer comprising fibroblasts and other cell types. In order to simultaneously obtain two distinct cultures of isolated keratinocytes and isolated fibroblasts from the same biopsy or skin piece, separation between the two skin layers should take place.

The step of obtaining isolated and separated cell cultures is crucial to the success of the following steps in the process of skin formation. Specifically, the presence of residual fibroblasts in the keratinocytes culture should be avoided.

After receiving the biopsy sample (optionally cut to pieces), the biopsy is processed in a cell preparation device/module. In one embodiment of the invention, the cell preparation device comprises at least two cell isolation apparatuses/chambers, wherein at least one apparatus designated for the isolation of single cell fibroblasts from the dermis pieces and at least one apparatus designated for the isolation of single cell keratinocytes from the epidermis pieces. In another embodiment, the cell preparation device comprises at least one cell isolation chamber, such that the entire cell preparation device is designated for producing either single cell fibroblasts suspension or single cell keratinocytes suspension.

Optionally, the cell preparation device further comprises at least one layer separation apparatus/chamber, to which the skin biopsy/piece(s) is inserted prior to its transfer into the cell isolation chamber.

After connection of the biopsy kit to the separation chamber or the isolation chamber, the skin biopsy or skin pieces are transferred to said separation chamber or isolation chamber. The transition of the skin fragments from the biopsy kit and into the cell preparation device requires a connection between the two compartments, for example, a sterile tube welding between the two or a sterile interface. It should be noted that the connection means have to be sterile in every case. The connection of the biopsy kit to the separation or isolation apparatus prevents the exposure of the cells to the environment and contributes to the automation of the process of producing skin grafts.

The commonly used technique for separating the dermis and epidermis layers involves manually pealing the epidermis layer by using forceps after the layer from the biopsy was suspended in a solution containing a separating enzyme, such as dispase, thermolysin or trypsin. This mechanical separation between the two skin layers poses a challenge to the successful automation of the process of producing skin grafts. Accordingly, the present invention provides several alternative solutions for efficient separation between the dermis and epidermis layers, as described below.

According to one embodiment of the invention, after the cutting of the biopsy into fine strips of skin, or small squares, the skin pieces are flushed or suctioned into a layer separation chamber where a solution comprising an enzyme, or a mixture of enzymes, that enables the separation of the dermis layer from the epidermis layer is introduced to the skin strips. A suitable exemplary enzyme for this purpose is selected from the group consisting of dispase, trypsin, thermolysin, or a mixture thereof but of course any other suitable enzyme can be used, as will be apparent to the skilled person. Introduction of the solution containing the enzyme to the separation chamber in the automated process described herein can be carried out, for example, by a peristaltic pump, a robotic arm or by any other suitable technique.

According to the invention, the temperature of the solution in the separation chamber at the time of introduction of the separating enzyme is adjusted according to the optimal temperature at which the separating enzyme is most active. According to one embodiment of the invention, said temperature is 37° C.

In some embodiments, the enzymatic process of separation between the dermis and epidermis layers is assisted by a stirrer, vortex or a gentle shake, in order to provide homogeneous enzyme distribution, ensuring constant contact of fresh and active enzyme with the edges of the skin strips, and applying shear stress to the skin layers, thus facilitating easy and efficient separation between the two skin layers. Following the enzymatic separation of the two skin layers, spatial separation of the dermis layer from the epidermis layer into two different chambers takes place. The invention provides several approaches to spatially separate the two skin layers.

According to one embodiment of the invention, sedimentation is employed. According to the sedimentation approach, since the epidermis layer is characterized by smaller density than the dermis layer, waiting for a prolonged time would lead to spatial separation between the two layers, where the more dense dermis layer fragments will remain sedimented at the bottom of the chamber while the less dense epidermis layer fragments will float towards the surface at the top of the separation chamber. The transfer of spatially separated dermis or epidermis layers into their respective chambers may be achieved, for example, by suction of the solution from the top of the separation chamber to retrieve the epidermis strips or at the bottom of the separating chamber to retrieve the dermis strips.

The dimensions of the separation chamber are also relevant to the efficiency separation process. According to one embodiment of the invention, the chamber in which the separation between the dermis and epidermis layers takes place is relatively narrow and high, in order to simplify the distinction between the two skin layers. In addition, increasing the volume of the solution inside the separation chamber would also contribute to the separation process of the two layers.

Figure 1:
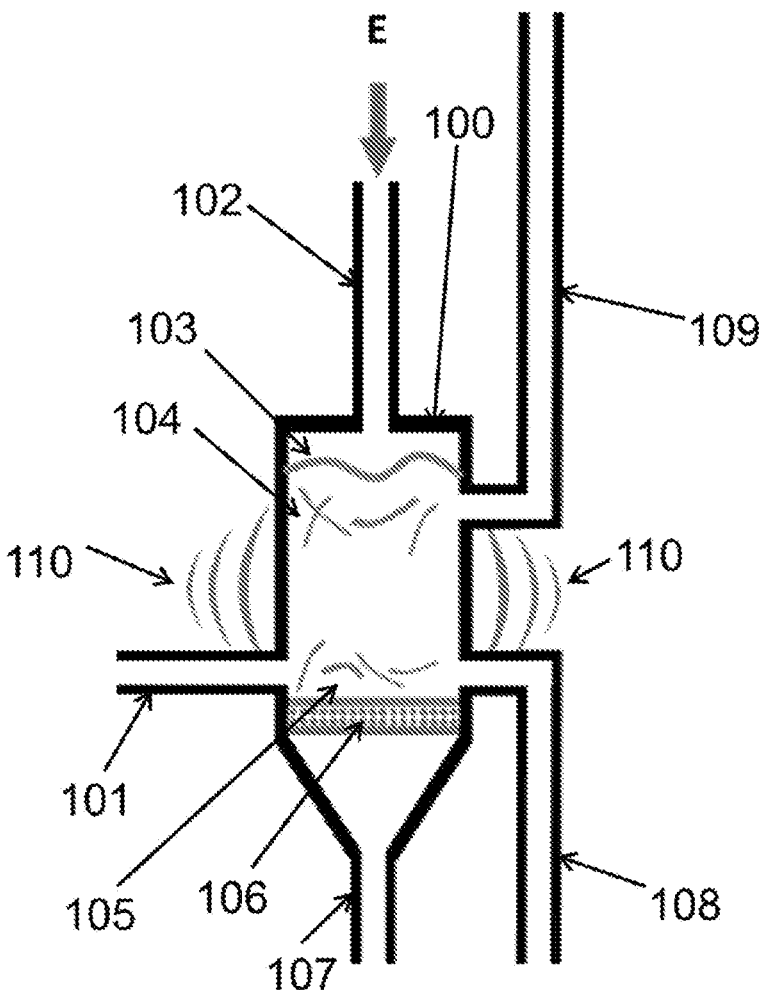
FIG. 1 is a schematic illustration of a separation chamber, assisted by an external agitation.

FIG. 1 is a schematic illustration of a separation chamber 100 assisted by external agitation 110. The cut skin strips are flushed into the separation chamber 100 through inlet 101. A solution containing the separating enzyme(s) (E) is introduced through inlet 102. External agitation of the separating chamber 100 results in the sinking of dense dermis strips 105 and the floating of less dense epidermis strips 104 in the total volume of the solution 103. Waste material passes through filter 106 and is removed from the separation chamber 100 through outlet 107. Following the separation between the two skin layers, the dermis strips 105 are transferred to one chamber through outlet 108, while the epidermis strips 104 are transferred to a second chamber through outlet 109.

Figure 2:
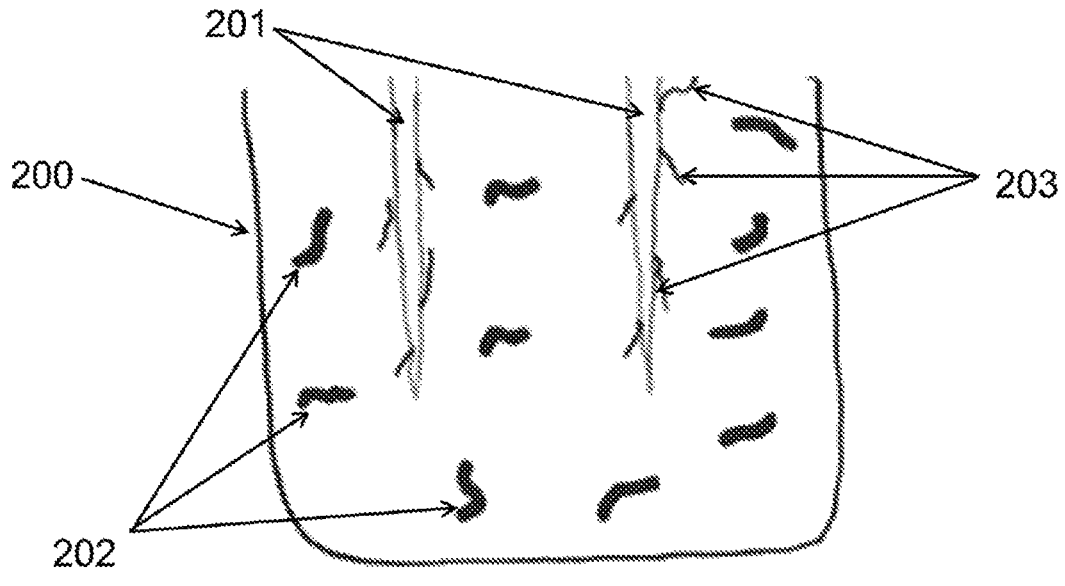
FIG. 2 shows an exemplary illustration of another separation process, according to another embodiment of the invention, illustrating the "fishing rod" approach.

The separation of the dermis and the epidermis layers can also be established by a "fishing rod" approach. FIG. 2 shows an exemplary illustration of another separation process, according to another embodiment of the invention, illustrating the "fishing rod" approach. According to FIG. 2, at least one plastic rod 201 is inserted into separation chamber 200 that contains a solution. Since the epidermis layer tends to adhere to plastic surfaces, the epidermis strips 203 that were detached from the dermis strips 202 by treatment with a separating enzyme as describe above, stick to plastic rods 201, while the dermis strips 202 remain suspended in the solution. Thus, extraction of plastic rods 201 from chamber 200 would lead to the removal of epidermis strips 203 chamber 200.

Following the separation between dermis and epidermis strips, plastic rods 201 can be placed in one chamber, where detachment of the epidermis strips 203 from rods 201 can take place, for example, by treating rods 201 with a solution comprising a suitable enzyme (such as trypsin). The remaining dermis strips 202 in the chamber 200 can be flushed or suctioned to a second chamber for further processing.

Figure 3:
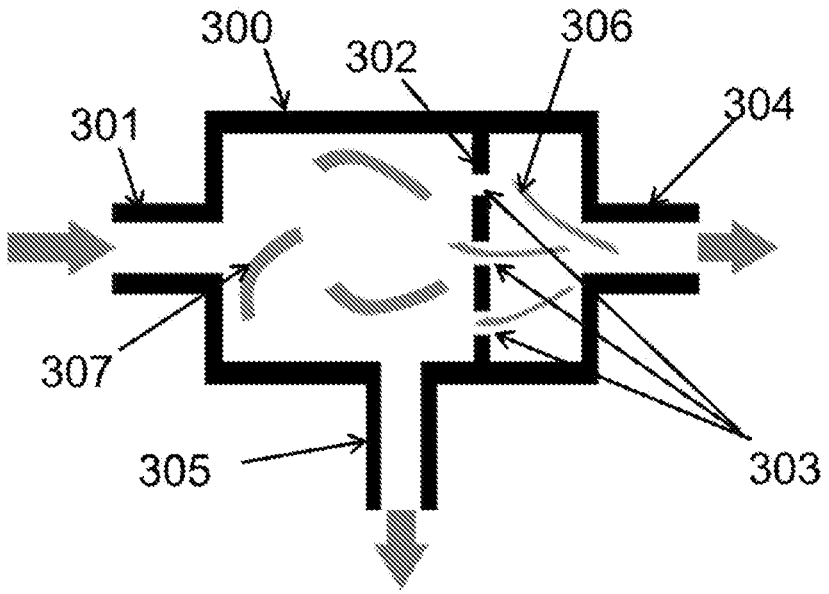
FIG. 3 is a schematic illustration exemplifying a filtration approach, which is based on the difference in rigidity of the two skin layers, where the layers are filtered through at least one membrane or grid, optionally with a pulsatile flow.

In yet a further embodiment of the invention, the dermis and epidermis strips that are detached from one another by treatment with a separating enzyme as described above, are filtered through at least one membrane or grid, optionally with a pulsatile flow, in order to achieve spatial separation between the two skin layers. FIG. 3 is a schematic illustration exemplifying such filtration approach, which is based on the difference in rigidity of the two skin layers. According to FIG. 3, each pulse of flow entering separating chamber 300 through inlet 301 pushes the thinner and more flexible epidermis strips 306 through narrow spaces 303 of the membrane 302, and out through outlet 304 into one chamber for further processing. At the same time, the thick dermis strips 307, which are not able to pass through membrane 302 are pushed out of chamber 300 through outlet 305 into a different chamber. As can be appreciated by a person of skills in the art, the separating chamber can also comprise more than one membrane or grid, in which the spaces of each membrane or grid can be of the same size or in different sizes than the first membrane or grid.

Figure 4:
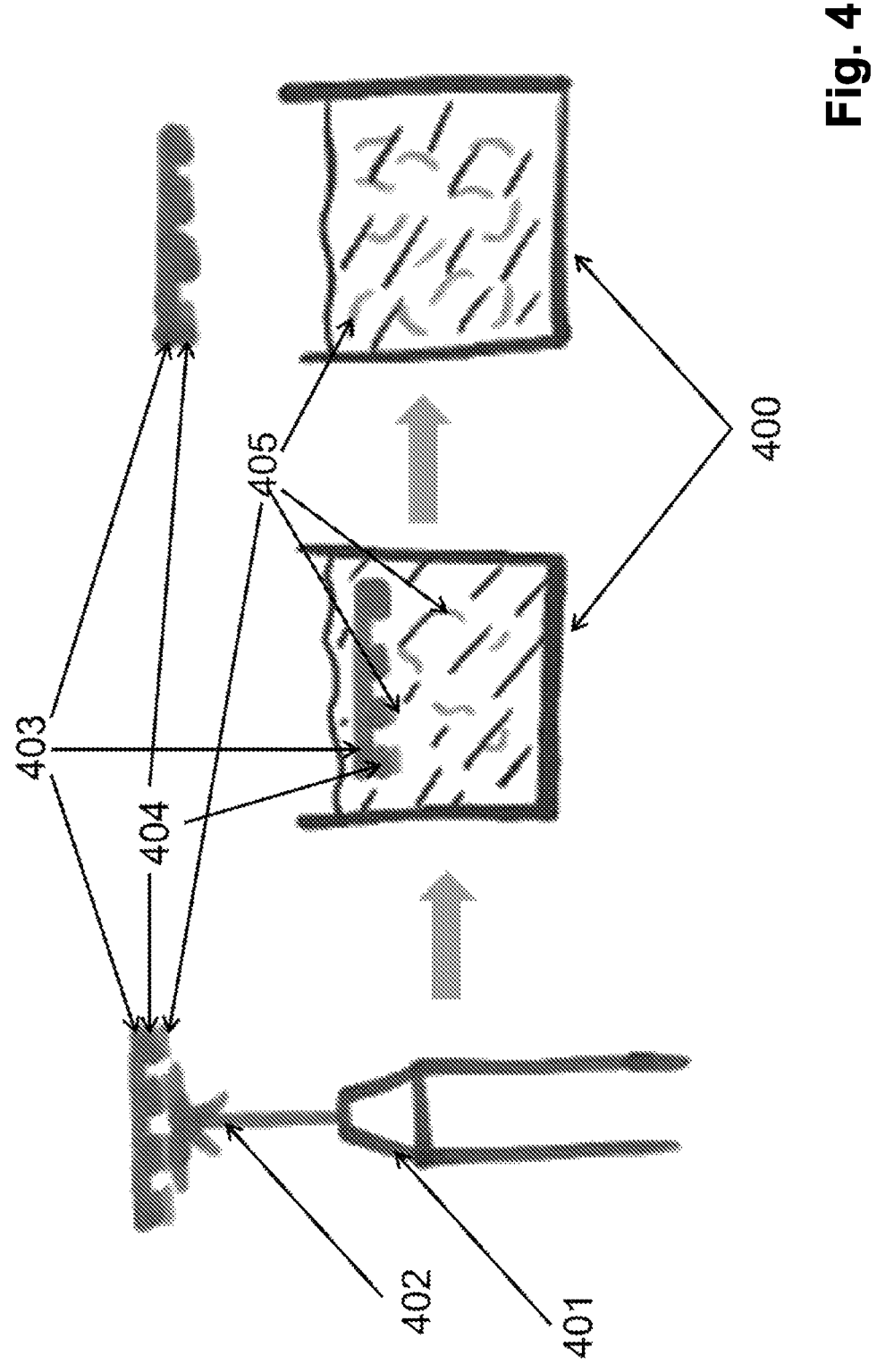
FIG. 4 is a schematic illustration exemplifying an approach, according to another embodiment of the invention, based on "laser engraving", utilized in order to achieve spatial separation between epidermis and dermis layers.

In another embodiment of the invention, an approach based on "laser engraving" is utilized in order to achieve spatial separation between epidermis and dermis layers. FIG. 4 shows an exemplary illustration according to this approach. According to FIG. 4, the skin biopsy is fixated to a fixing surface 403 in a specific orientation such that the dermis layer is in contact with the fixing surface 403, while the epidermis layer is facing away from the fixing surface 403. A laser gun 401 shoots a laser beam 402 to the skin biopsy to cut skin to fine strips. The assembly of the fixed tissue is transferred into a separation chamber 400, containing a solution comprising a separating enzyme. The epidermis strips 405 detach from the dermis strips 404 and are suspended in the solution in the separating chamber 400. Fixing surface 403 carrying the dermis strips 404 is then removed from chamber 400 and placed in a new chamber for further processing of the dermis strips. The suspended epidermis strips 405 can be flushed to a different chamber for further processing. In a specific embodiment of the invention, the intensity of the laser beam is adjusted to selectively cut only the epidermis layer, while leaving the dermis layer intact. Thus, when the assembly of fixed tissue comes in contact with the solution containing the separating enzyme, the perforation of the epidermis layer allows the separating enzyme to reach the basement membrane residing between the epidermis and dermis layers and catalyze the separation between the two layers. Cutting and further processing of the dermis layer can take place after spatial separation of the dermis layer from the epidermis layers.

In yet another embodiment, a dermis biopsy is taken separately from an epidermis biopsy and the layers are placed into two independent biopsy boxes/kits, such that spatial separation between the two skin layers is achieved prior to entering the automated system for producing skin grafts. For example, applying pressure, heat, or a combination thereof at the time of harvesting of the biopsy (either directly on the patient or on the biopsy after harvesting) will make the skin form blisters which can be manually cut away, thus mechanically separating the epidermis from the dermis. In case this procedure is performed directly on the patient, the corresponding dermis piece is then removed using conventional surgical methods, for example by using a dermatome.

The term "skin biopsy" as used herein refers to a sample of tissue comprising at least one of the two outer layers of the skin, namely, tissue of the epidermis layer only, tissue of the dermis layer only or tissue of both the epidermis and dermis layers. A tissue sample comprising the dermis layer together with at least a portion of the deeper skin layers (for example, the hypodermis layer) is also encompassed by this term.

Throughout the separation process, and in any stage that involves fluids, the amount of fluid needs to be suitable to each desired process. One way of controlling fluid amounts is by using a volumetric pump. Other suitable methods are well known to the skilled person and, therefore, are not discussed herein in detail for the sake of brevity.

Each compartment of the system, particularly compartments that are used for cell amplification, needs to be occasionally filled with fresh medium. According to one embodiment of the invention, each compartment is connected to a medium source that is sequentially filled, and several compartments can be connected to the same source. When using a gel mixture, gelling starts reacting immediately when the components of the collagen gel are mixed. Therefore, the mixing should occur shortly before introducing it into the growth chamber. According to another embodiment of the invention, the system comprises static mixers that use a series of static flow dividers or guide vanes to mix two or more fluids.

The system according to the invention comprises a subsystem of liquid management. Said subsystem controls the operation of the media sources and the fluid compartments. In addition, this subsystem controls the storage conditions of medium or other liquids by taking under consideration the specific requirements of each one. It also controls the management of fluid waste. Indicators for filling or taking out materials from every apparatus can be based on different sensors, such as concentration sensors of different materials (in any state of matter), or it can be based on timing schedules, or be operated by an operator. The liquid management subsystem can be comprised of sterile components and aseptic connectors or connecting means, but in case of a non-sterile interface, the materials can be sterilized before entering the different compartments, for example, by steam or UV radiation. The liquid management subsystem is controlled so that all its conditions, such as temperature and humidity, would be suitable for each material. The subsystem is also suitable to contain frozen material.

Following spatial separation between the dermis and epidermis layers of the skin, but prior to cell proliferation/expansion step of the automated process for producing skin grafts, a suspension containing isolated single cells is needed. According to the invention, extraction of fibroblasts from the dermis strips is achieved enzymatically and/or by shredding the dermis strips. It should be noted that an example of a product enabling the shredding of tissue pieces into single cells in a disposable is the "gentleMACS Dissociator" produced by Miltenyi biotech. This device features a plastic disposable tube including static teeth and a rotor guiding the tissue to them. Due to the exactly specified gap, a solution with viable cells can be achieved. However, the product is only intended for manual operation. Accordingly, the invention provides various approaches for shredding of the dermis in a module that is integrated in the automated system for producing skin grafts.

In some embodiments of the invention the shredding of the dermis strips is carried out by knives operating in a feed channel until a homogeneous paste is produced. The knives repeatedly hit the dermis and ultimately disintegrate it.

Figure 5:
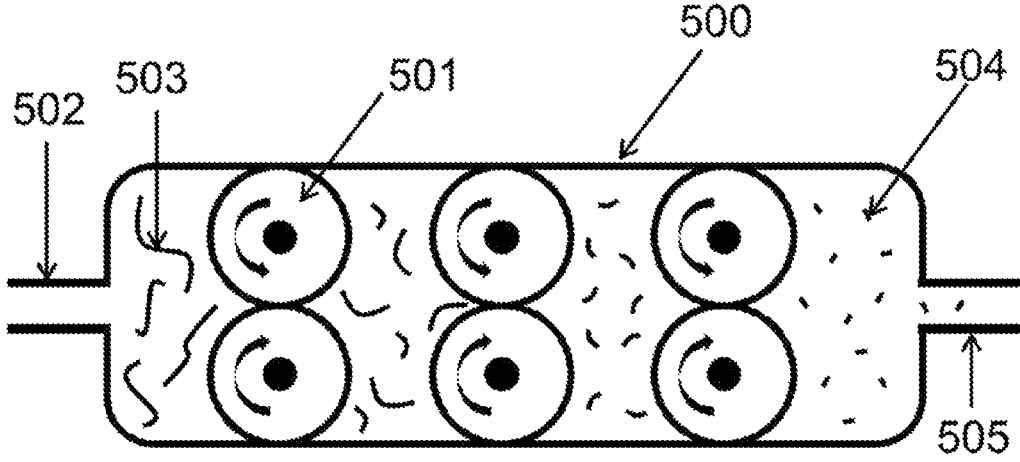
FIG. 5 is a schematic illustration of an isolation chamber, according to another embodiment of the invention, comprising a set of rolling knives.
Figure 6:
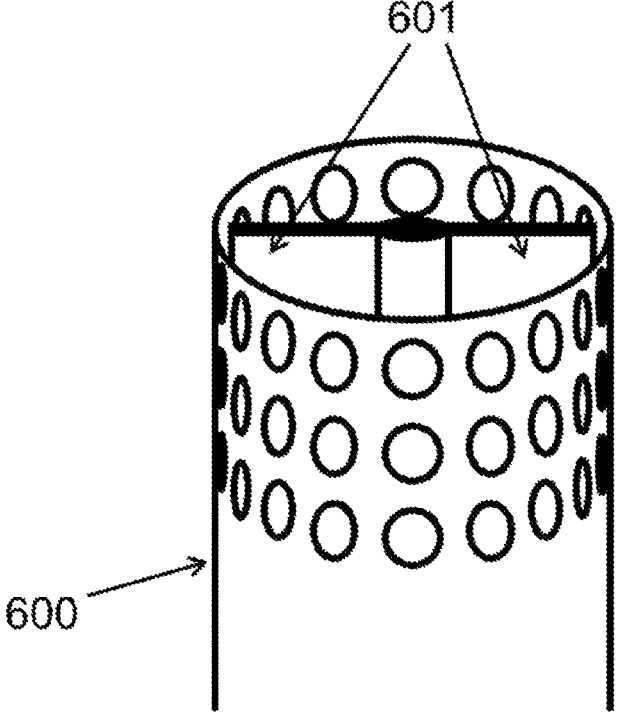
FIG. 6 is a schematic illustration of another example of isolation chamber, according to another embodiment of the invention comprising counter-rotating knives.

In another embodiment, the knives are operated in a rotating manner. According to a specific embodiment, the knives are operated in a counter-rotating manner. FIG. 5 is a schematic illustration of an isolation chamber 500 comprising a set of rolling knives 501, wherein dermis strips 503 are introduced through inlet 502. As the dermis strips 503 pass through the set of knives 501 arranged, for example, as multiple pairs, single fibroblasts 504 are extracted and exit isolation chamber 500 through outlet 505 for further processing. The rotation direction of knives 501 is indicated by the curved arrows. FIG. 6 is a schematic illustration of another example of isolation chamber 600, comprising counter-rotating knives 601.

According to some embodiments of the invention, a solution containing a suitable isolating enzyme, such as collagenase, is added to the dermis strips prior to, during or after the shredding. In other embodiments, the dissociation of dermis strips into fibroblasts is conducted strictly enzymatically. The enzymatic extraction of fibroblasts may be performed a single time or multiple times. In one embodiment, exposure of the dermis strips to the enzyme is combined with agitation, for example, shaking or stirring.

According to a specific embodiment, fibroblasts are dissociated from the dermis strips by a single prolonged exposure (for example, 12-24 hours) to an isolating enzyme at an optimal temperature for the activity of the enzyme, for example 37° C., without any shredding. Mechanical agitation of the isolation chamber is carried out at least at the very end of the exposure period to the isolating enzyme, for example, during the last hour of the exposure period.

According to one embodiment of the invention, fibroblasts are extracted from dermis strips by first shredding the dermis and then addition of an isolating enzyme solution. After a suitable incubation time at an optimal temperature for the activity of the enzyme, for example 37° C., optionally combined with agitation, the dissolved fibroblasts are flushed through a filter, to retain the remaining collagen and other debris, by means of adding a suitable medium for expansion of human fibroblasts, termed here "FM". In a specific embodiment, the process of adding the enzyme, incubating and flushing is repeated multiple times, for example, four times.

Figure 7:
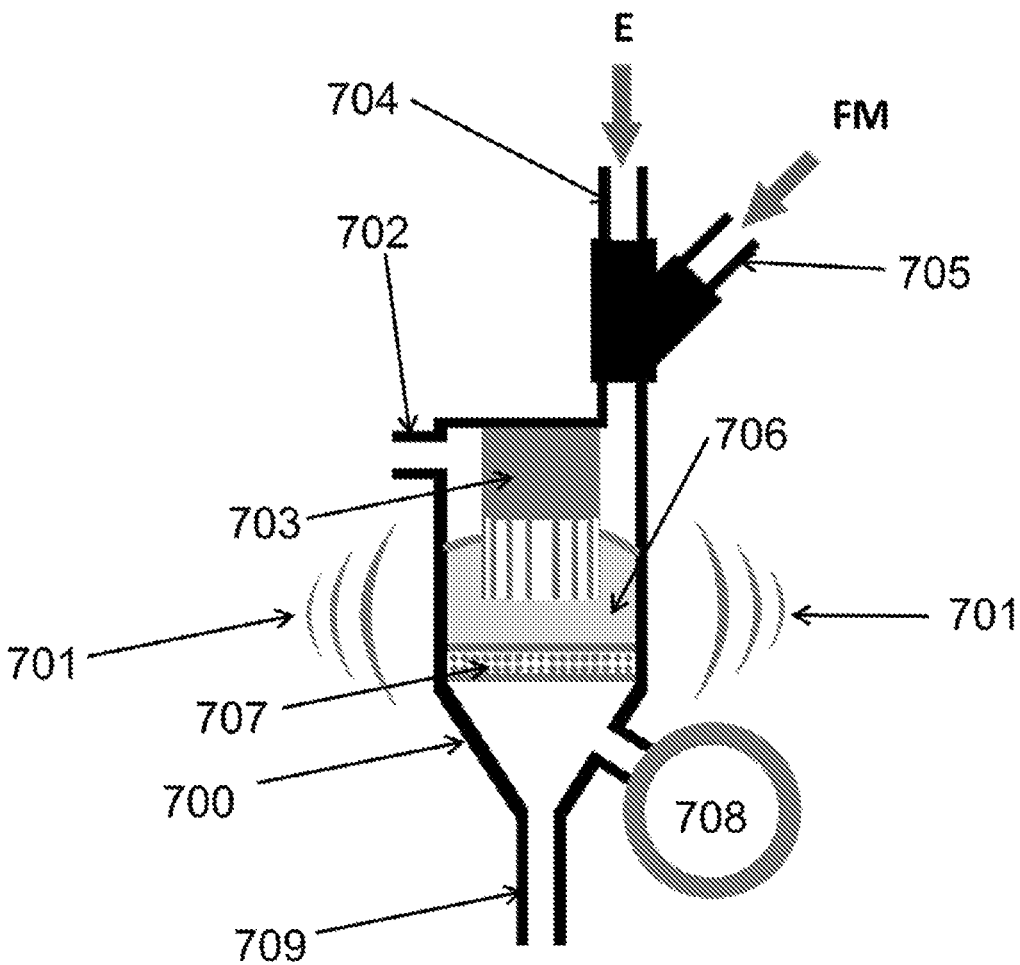
FIG. 7 is a schematic illustration of a cell isolation chamber, comprising a shredder, according to one embodiment of the invention.

FIG. 7 is a schematic illustration of a cell isolation chamber/apparatus comprising a shredder, according to one embodiment of the invention. Dermis strips (not shown) are flushed or suctioned into a cell isolation chamber 700 through inlet 702. A shredder 703 that comprises rotating knives is operated. Then a solution containing a suitable enzyme (E) is introduced to the dermis solution 703 through inlet 704 in combination with external agitation 701. After suitable incubation time, FM medium is introduced through inlet 705 and combined with suction from the bottom of chamber 700 by vacuum apparatus 708, and isolated fibroblasts are flushed through filter 707 and exit through outlet 709 to a new chamber for further processing. In one embodiment, the FM medium comprises serum, for example fetal bovine serum (FBS), which may be necessary for blocking the activity of the isolating enzyme (such as trypsin) and thus prevent the cells from being exposed to the isolating enzyme for undue duration.

In parallel to the isolation of single fibroblasts from dermis strips, isolation of single keratinocytes from epidermis strips takes place. In one embodiment of the invention, the epidermis is subjected to a suitable isolating enzyme, such as trypsin, in order to obtain isolated keratinocytes, optionally in combination with agitation, such as stirring or shaking. As was described for fibroblasts isolation, the isolation of keratinocytes form epidermis fragments may be carried out in an isolation chamber adapted for this purpose, in which the epidermis fragments are incubated in a solution comprising at least one isolating enzyme. After suitable incubation time with the isolating enzyme, keratinocyte medium (KM), optionally comprising serum, is introduced to the solution and the isolated keratinocytes are transferred to a new chamber for further processing.

According to some embodiments of the invention, the automated process for isolating single fibroblasts or keratinocytes from dermis or epidermis strips, respectively, is designed so that already isolated cells are fed away from the active enzyme, either continuously or in regular intervals to an intermediate "depot". The intermediate depot may serve as a checkpoint for cell density and viability, such that keratinocytes or fibroblasts continue to be isolated until the number of viable cells in the intermediate depot meets the requirements for the subsequent step of cell expansion. In some embodiments, before introduction of fibroblasts or keratinocytes into the cell proliferation/expansion device/chamber, the cell solutions are filtered. In addition, the solutions resulting from the fibroblasts and keratinocytes isolation chambers, which contains a "slurry" of isolated cells in suspension, isolating enzymes and medium containing serum need to be washed and the isolated cells need to be concentrated in order to achieve suitable cell density for cell expansion. In one embodiment, concentration of isolated fibroblasts and keratinocytes is carried out by centrifugation of the solution, resulting in dense pellets, which after discarding of the supernatant are suspended in fresh culture medium (FM or KM, respectively) at a desired concentration. Alternatively, the concentration of the cells can be achieved by flow filtration (filter design). The filter design comprises at least one membrane to retain cells at one side of the membrane while the solution passes though the membrane. Thus, the cells will be suspended in decreased volume of liquid. Additional membranes having varying pore sizes can be used to obtain a suspension of single cells separate by retaining large pieces of tissue or cell aggregates and letting only single cells to pass through the membrane. The filter design is also suitable to be used for any medium exchange.

Figure 8:
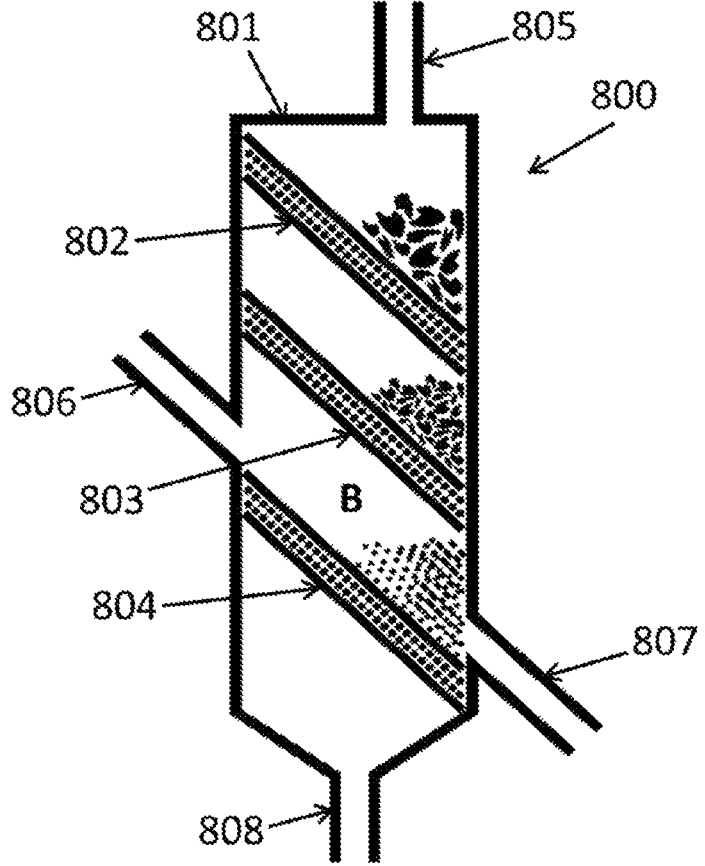
FIG. 8 is a schematic illustration of a filter design, according to another embodiment of the invention.

FIG. 8 is a schematic illustration of a filter design 800, according to one embodiment of the invention. The filter chamber 801 typically comprises an inlet 805 for introducing the suspended slurry and an outlet 808 for waste liquid. The chamber 801 also comprises three membranes, such that membrane 802 has the largest pore size of the three and membrane 804 has the smallest pore size of the three, thus allowing only single cells to reach the backwash area (B). Membrane 804 retains the cells while letting liquids pass through, thus concentrating the cells. Then, the concentrated single cells can be transferred to a new chamber for further processing, for example, by a flushing solution introduced to the backwash area B through backwash inlet 806 and out through backwash outlet 807.

In other embodiments, branching of the cell path of the keratinocytes is supported for a future inclusion of various cell types, such as melanocytes, in the overall process.

FIG. 9 is a schematic overview of separation and isolation chambers, according to one embodiment of the invention. The various elements shown in the figure are of course only illustrative, as will be easily understood by the skilled person, and different arrangements of components can be provided. The following is a brief overview of the functions of the first module, according to the numerals shown in FIG. 9:

Docking of the Biopsy Kit to the Cell Preparation Device (1)

The Biopsy Kit 901 is connected to the cell preparation device 900 and the biopsy is flushed to the preparation device 900. Optionally, the skin is cut into smaller pieces. This helps to increase the area where the enzyme separating between the layers or isolating the cells can engage the layer boundary and therefore decrease the processing time. In the specific embodiment shown in FIG. 9, skin pieces are transferred from the Biopsy Kit 901 to separation chamber 904 by flushing, such that flushing liquid is introduced to Biopsy Kit 901 through inlet 902 and exit with the skin pieces through outlet 903 into separation chamber 904.

It should be noted that the biopsy should be disinfected, ideally sterile, and this can be achieved, e.g., by washing it with a bacteriocidic washing solution and/or other anti-microorganism agents, such as anti-yeast or anti-fungal agents (e.g., amphotericin B). This can either already occur in the Biopsy Kit 901 during transport or at any point in the system before separation of the layers. Washing can also be supported by movement such as stirring or shaking.

Layer Separation and Layer Division (2)

Separating and dividing epidermis and dermis can be achieved in one embodiment of the invention by adding the enzyme dispase to the uncut skin and subsequently pulling the epidermis from the dermis. The process of layer separation can be supported by stirring or shaking to provide a homogeneous enzyme distribution. The goal is to separate the two layers spatially into different chambers. Enzyme solutions, washing solution or other media can be introduced into separation chamber 904 through inlet 905 and exit (after filtration) through outlet 906. Optionally, a portion of the waste can be collected in retention bag 907 for quality control, such as sterility testing, or other measurement. After appropriate time has passed for the separation enzymes to work, and the epidermis layer (floating at the top of the chamber) is separated from the dermis layer (sinking to the bottom of the chamber), the layers are transferred to their respective chambers. This transfer can be achieved, for example by flushing or suction of the epidermis pieces through outlet 908 into the keratinocyte isolation chamber 910 and of the dermis pieces through outlet 909 into fibroblast isolation chamber 911.

Isolating Keratinocytes (3)

The epidermis is subjected to the enzyme trypsin or TrypLE to isolate keratinocytes. Again, stirring or shaking facilitates this step. Any fresh solution or media can be introduced to the keratinocyte isolation chamber 910 through inlet 912 and exit through an outlet (such as the outlet depicted at the bottom of chamber 910 in the figure). A vacuum apparatus (V) may assist in removing waste materials.

Shredding the Dermis and Isolating Fibroblasts (4)

In case of fibroblasts, the isolation of cells from the dermis layer can be enhanced by thoroughly shredding the dermis, until a homogeneous paste is produced. Approaches to the mechanical shredding include rotating knives, repeatedly hitting the dermis and ultimately disintegrating it. The actual enzymatic extraction may be performed multiple times, as this might result in more favorable kinetics. As for keratinocyte isolation chamber 910, the fibroblast isolation chamber 911 may also include inlet(s) and outlet(s) for entry and exit of solutions, as well as a vacuum apparatus (V).

Exchanging the Medium (5)

The keratinocytes and fibroblasts, each in their own chamber, are suspended in KM (keratinocytes medium) and FM (fibroblasts medium), respectively, for further processing and cultivation. At multiple locations in the production process, the medium in which the cells are suspended may need to be exchanged. This may be implemented for example by centrifugation or flow filtration in centrifuge/filter design 913, resulting in dense pellets which are then introduced to the new solution and resuspended. Concentration of the cells can also be achieved by resuspending the cells in a volume of medium that is lower than the volume in which the cells were suspended prior to the medium exchange.

Counting the Cells (6)

Optionally, the number of both keratinocytes and fibroblasts is determined by cell counter 914. As a minimum cell density on the fixed surface in the cell bioreactor is required, it may be necessary to include a preliminary expansion step before inserting the cells in the cell bioreactor if the cell count is too low.

Providing a Liquid Sample (7)

At multiple points, a liquid sample may be provided for quality control such as sterility test. In such case, the liquid is collected in retention bag 907 and removed from the system for performing the desired test. Removing this retention bag 907 can be done in an aseptic manner, such as by using a sterile tube sealer or other suitable means for aseptically removal of the retention bag.

Filtering the Cells (8)

Before introduction into the cell expansion device/bioreactor, the cell solutions may be filtered using filter 915 to avoid clogging by cell aggregates.

In a next stage, both fibroblasts and keratinocytes need to be cultured and proliferated to enable the production of grafts with a significantly larger area compared to the biopsy. The cell expansion represents a crucial step in the process for producing skin grafts, as this step needs to guarantee that the number of cells is sufficient for the production of the needed skin graft area. Generally, the needed cell expansion time is defined by the needed number of cells for production and the number of extracted cells from the biopsy, as well as the specific biological characteristics of the cells.

According to one embodiment of the invention, expansion of keratinocytes takes place in a dedicated expansion device or bioreactor, where keratinocytes are cultivated until a sufficient amount for the grafts is available. In parallel, isolated fibroblasts are cultivated in another expansion device.

An example of a product that enables cell expansion is the "Quantum" device from Terumo BCT. Quantum is an automated platform designed to simplify the open, labor-intensive tasks associated with manual cell culture. The Quantum process is functionally closed, reproducible, and scalable with disposable parts. The flexible system allows the optimization and configuration the cell culture process.

After exiting the cell expansion device, keratinocytes and fibroblasts are processed and prepared for the introduction to the tissue formation device.

According to the present invention, upon finishing the cultivation of fibroblasts, the required number of cells is pumped into the tissue formation module, optionally after the medium is exchanged. The required number of cells is determined individually for each patient, since different patients require different areas of grafts and therefore different cell numbers. According to one embodiment of the invention, the ratio between the number of fibroblasts and the number of keratinocytes to be seeded in the tissue formation device is about 1:5 to about 1:12, specifically about 1:7 to about 1:10. In a non-limiting example, about $1.5 \times 10^6$ to about $3 \times 10^6$ fibroblasts and about $12.5 \times 10^6$ to about $16 \times 10^6$ keratinocytes are transferred to the tissue formation device to produce a full-thickness skin graph having an area of about 100 cm$^2$ during about 10-16 days. Of course, the number of cells to be transferred to the tissue formation module can vary as a result of process optimization, such as changing the content of FM and/or KM.

Figure 10:
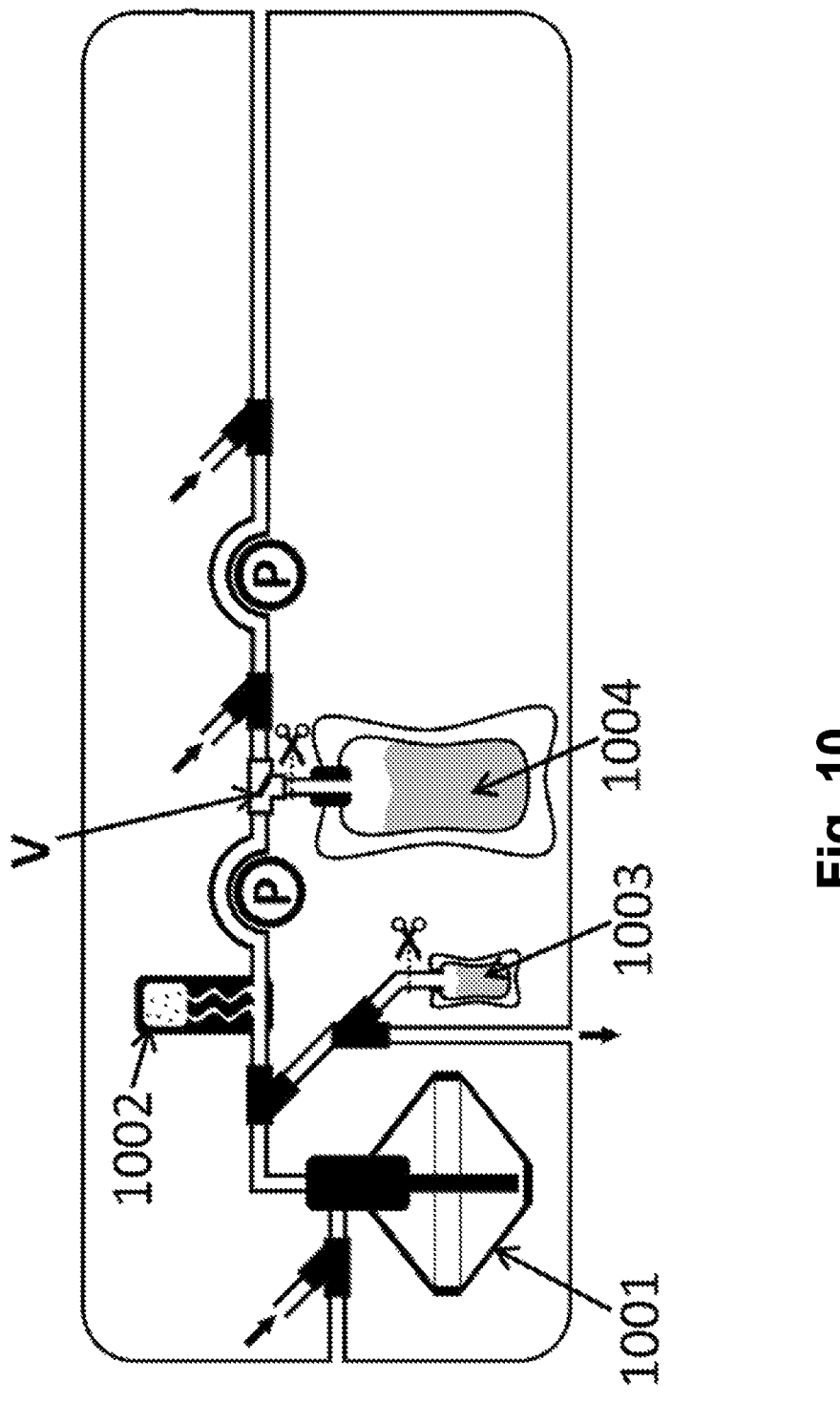
FIG. 10 is a schematic overview of fibroblasts post-expansion processing device, according to one embodiment of the invention.

FIG. 10 is a schematic overview of fibroblasts post-expansion processing device/module, according to one embodiment of the invention. Upon finishing the cultivation of fibroblasts, the medium has to be exchanged in device 1001 that is configured to carry out the procedure known as cell-wash and (optionally) concentration. Several commercial devices are available on the market, which can be suitably utilized for this purpose, such as the GE Healthcare Sepax C-Pro and the Fresenius-Kabi LOVO. Subsequently, the cells are counted in cell counter 1002 to confirm the required number has been reached. Fresh medium or a specific solution or buffer can be introduced by inlets marked by ingoing arrows. Waste is removed from the post-expansion processing device by outlets marked by outgoing arrows. Retention bag 1003 can be used to collect liquids from the device for purposes of quality control checks. Additionally, cell retention bag or "check out" bag 1004 can be used to collect a cell sample for banking or other quality control checks. The cells can be directed either through the device or into bag 1004 by mean of a valve (V), typically a stopcock valve. The device can also be equipped with at least one volumetric pump (P) to ensure the flow of cell suspension through the device (or into retention bags).

As appreciated by a person of skills in the art, the process of changing cell culture medium may include a washing step and/or a cell concentrating step, which may be implemented by centrifugation or flow filtration of the cell solution, resulting in dense pellets, which after discarding of the supernatant are suspended in fresh culture medium at a desired concentration.

Keratinocytes are processed in a similar manner as fibroblasts. However, since the cultivation of keratinocytes is estimated to take a few days less, interim freezing of keratinocytes may be necessary. Freezing requires two additional medium changes, as damage by freezing can only be avoided by suspending the cells in a specialized freezing medium. Notwithstanding the above, the freezing step can be omitted, if either the cultivation of keratinocytes is slowed down, or the cultivation of fibroblasts is sped up.

It should be noted that the delay in the expansion of keratinocytes also needs to take into account that the keratinocytes are only introduced to the tissue forming module at least about five days after fibroblasts. Thus, freezing of keratinocytes should be determined individually according to the patient. Furthermore, it may be beneficial to freeze keratinocytes (as well as fibroblasts), in order to halt the process for a desired duration, thereby having an additional method of timing the production process. The decision to freeze the cells and the freezing duration may also depend on the scheduling of the grafting procedure or the availability to treat the patient. Cell freezing may also serve to store them in a biobank for potential future graft manufacturing (for example, for prophylaxis purposes).

Figure 11A:
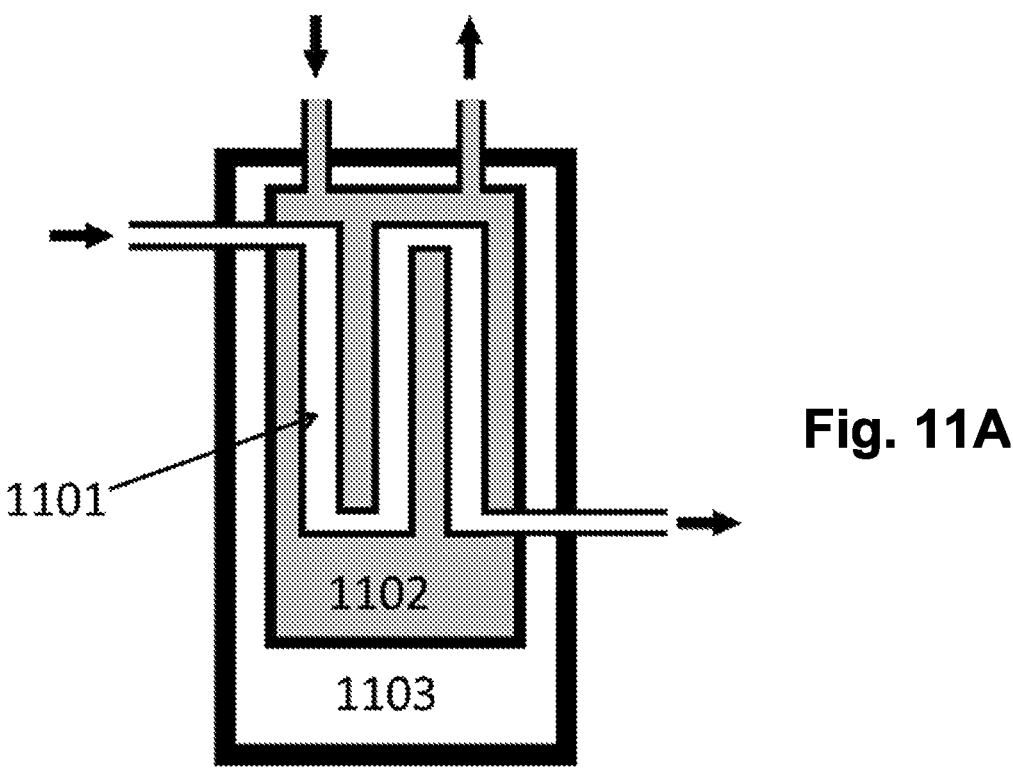
FIGS. 11A and 11B are schematic illustrations of specialized chambers for freezing and thawing, according to one embodiment of the invention.
Figure 11B:
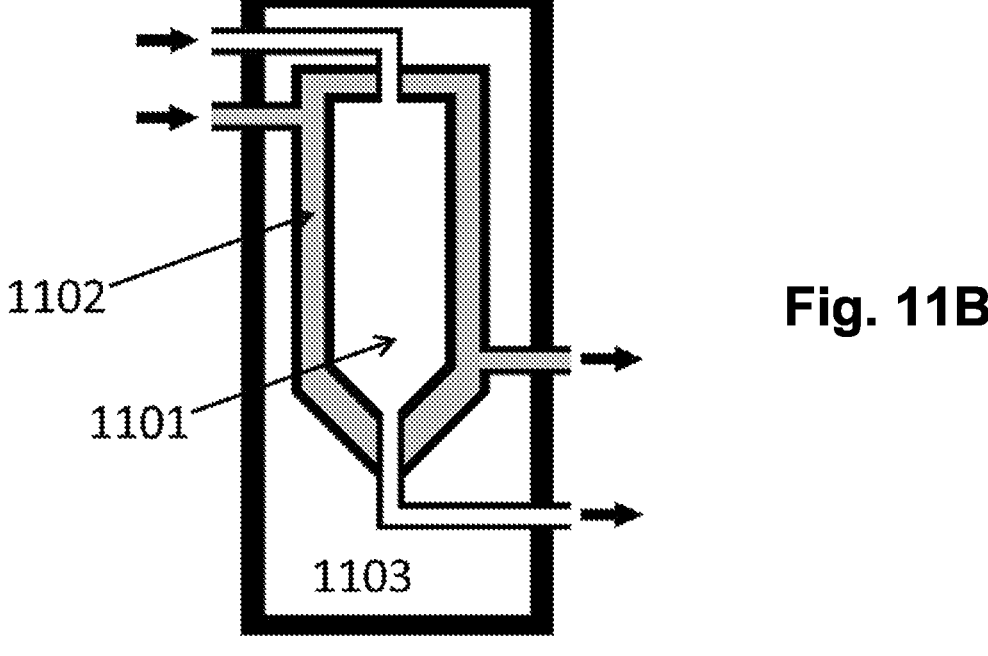

According to one embodiment of the invention, automated freezing and thawing occur in a specialized chamber with carefully controlled and logged cooling rates in order to avoid cell damage. This chamber consists of a disposable inlay with a large surface area, to enable quick heat transfer and avoid broad temperature distributions within the cell. FIGS. 11A and 11B are schematic illustrations of specialized cells for freezing and thawing, according to one embodiment of the invention. Inlay 1101 includes a heat exchanger 1102 through which a heating or cooling medium at a specific temperature is pumped with a carefully controlled flow rate. On the other hand, the cooling chamber 1103 is part of the non-disposable part of the module. The complete cell is well insulated. Inlets for inlay 1101 and heat exchanger 1102 are marked by ingoing arrows and the respective outlets are marked by outgoing arrows.

According to one embodiment of the invention, cell count and viability analysis are performed before the freezing process starts. In addition, cell count and viability analysis should be performed after a thawing process is finished. The process may not continue if the number of viable cells does not fulfill the requirements.

Figure 12:
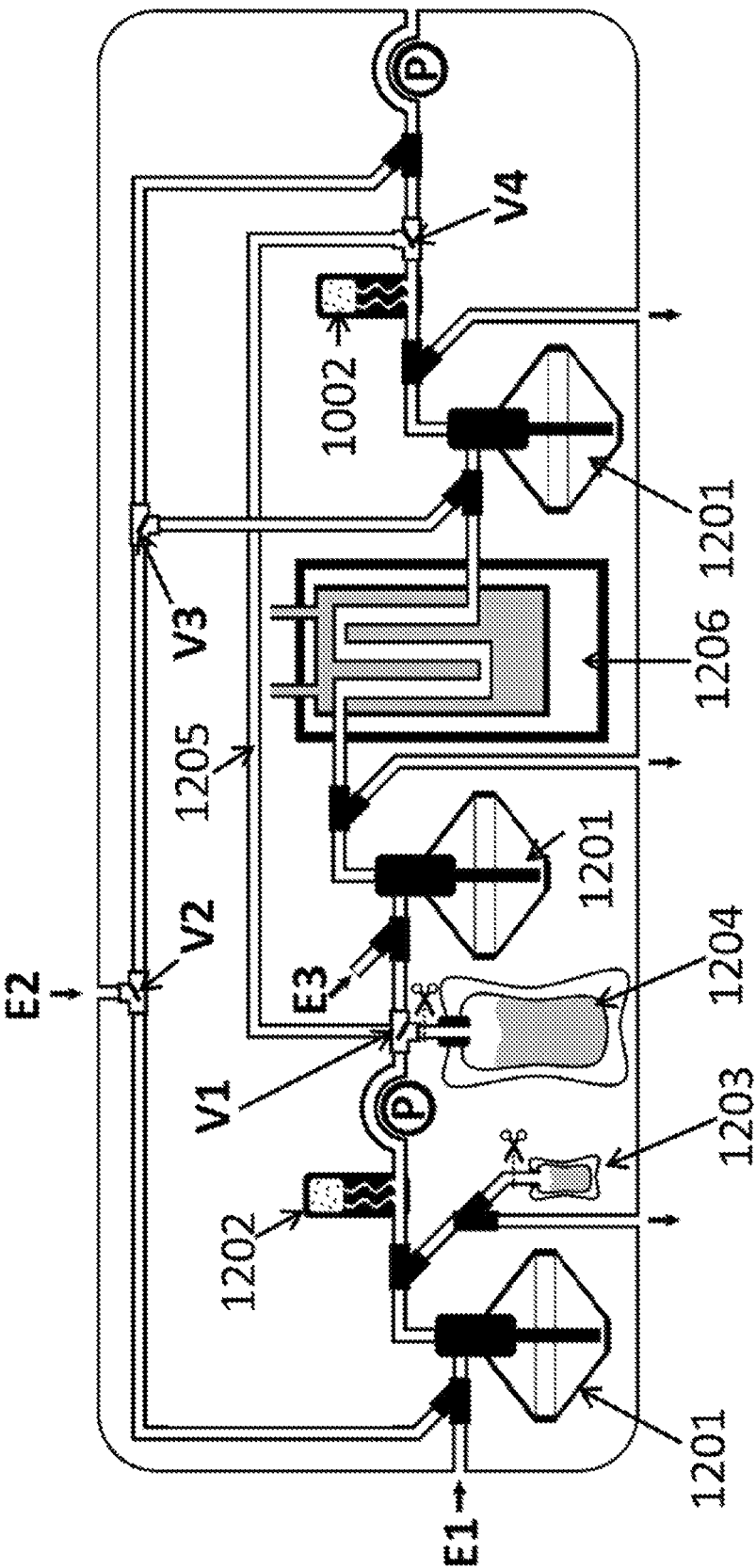
FIG. 12 is a schematic overview of keratinocytes post-expansion processing device, according to one embodiment of the invention.

FIG. 12 is a schematic overview of keratinocytes post-expansion processing device/module, according to one embodiment of the invention. Keratinocytes enter the post-expansion device through entrance E1. The cells may be washed and concentration in centrifuge/filter design 1201 and/or counted in cell counter 1202, and/or a liquid sample can be collected in retention bag 1203. Keratinocyte medium (KM) is introduced through entrance E2 and directed through valves V2 and V3 to different compartments in the post-expansion device. A valve (V1) can control whether the cells would be sampled in check-out bag 1204 or proceed to further processing. When interim freezing of keratinocytes is necessary for timing reasons, the cells would be directed through valve V1 to be freezing/thawing chamber 1206. Before entering chamber 1206, the medium should be replaced in centrifuge/filter design 1201 with suitable freezing medium introduced through inlet E3. After thawing and prior to proceeding into the tissue formation device, the cryopreservation medium should be replaced with fresh KM in centrifuge/filter design 1201 and optionally counted in cell counter 1202. Then the cells can be directed by valve V4 into the tissue formation device. The freezing step can be omitted, if either the cultivation of keratinocytes can be slowed down, or the cultivation of fibroblasts can be sped up. In this case, the cells are directed by valve V1 directly into the tissue formation device through a short track tube 1205. The device can also be equipped with at least one volumetric pump (P) to ensure the flow of cell suspension through the device (or into retention bags).

As can be appreciated by a skilled artisan, fibroblasts may also undergo post-expansion processing by the device shown in FIG. 12.

As mentioned above, after cell expansion, cells can be diverted out of the process for several purposes, such as cell banking, retention and/or storage of excess cells. For this purpose, a "check-out" bag may be available, which can be dosed and filled with the aid of a volumetric pump. The cells that are further processed are forwarded by valve. The bag is taken out of the automatic system and processed manually. The bag can be aseptically disconnected using for example a suitable tube sealer or other means in order to avoid compromising (i.e., exposing to the environment) the content of the system and avoid contamination.

It should be noted that the cells, i.e., fibroblasts, keratinocyte, or a combination thereof can be applied (for example, sprayed) directly on a wound area on a patient's skin in order to treat the wounded skin and rehabilitate it. The cells can be applied immediately after exiting the cell isolation device, or after undergoing at least one some degree (such as at least one passage) of proliferation in the cell expansion device.

According to the invention, in addition to the above described chambers, channels devices and modules, a shared periphery will control and coordinate the modules, and supply them with the required fluids. A modular structure is beneficial, as it simplifies the development of single modules, as well as maintenance and possible future alterations, including additional cell lines such as melanocytes. Therefore, interfaces between the different modules should support an exchange and addition of modules. These interfaces include suitable means for connecting fluidic systems, ideally by using aseptic connection means, or by aseptically disconnecting the products of each module, such as a liquid retention bag or a cell retention bag containing the desired cell suspension, and aseptically connecting it to another module using similar means of connection. This transfer of product bags from one module to the other can be either done manually or by using automated methods such as robotic systems. The modular approach also allows to "free" modules for another patient once the module has been used (and cleaned/sterilized), therefore allowing the potential treatment of multiple patients simultaneously with minimized equipment (rather than an entire line assembly dedicated to a single patient until a graft is ready for transplantation).

Figure 13:
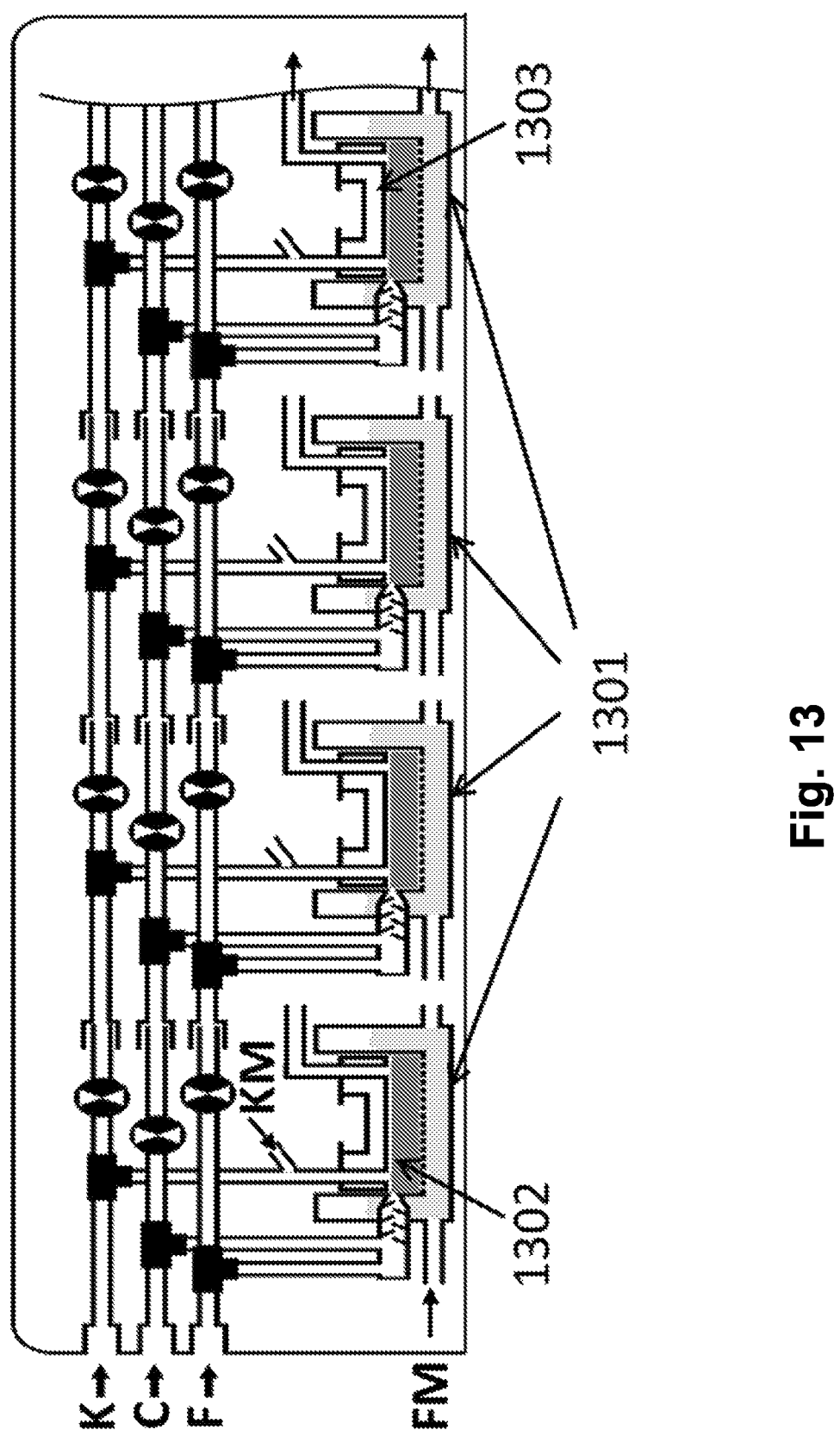
FIG. 13 schematically shows a tissue formation device according to the invention.

The invention further comprises a tissue formation device/module, which receives keratinocytes and fibroblasts in a solution, as well as cell culture media and necessary solutions. FIG. 13 shows an exemplary schematic formation device, according to one embodiment of the invention. The tissue formation device comprises at least one tissue forming chamber 1301. In each chamber 1301, collagen solution (C) is mixed with the fibroblasts (F) (in FM, supplemented with reconstitution buffer) and used to fill the culture compartment 1302 in order to obtain a hydrogel scaffold. The collagen hydrogel is then temporarily compressed by pressing lid 1303 down. The gel is cultivated for about five days or more. Subsequently, the keratinocytes (K, in KM) are seeded on top of the gel. The gel is cultivated for additional five days or more. During this process, fresh cell culture media should be supplied (KM on the top and FM on the bottom of the tissue or a single type of medium, for example, a mixture of KM and FM, is provided to all cells), old media removed and the pH level of the solution controlled by continuous exchange of air enriching with $CO_2$. Outlets for waste materials or samples are marked by outgoing arrows. After tissue cultivation, the graft can be transferred to a disposable vessel suitable for graft transport. Alternatively, the chamber 1301 can be sealed and removed from the tissue formation device, thus converting into a transport vessel. The tissue is of course kept under sterile conditions at all times during transport to the hospital where the grafting is carried out. As shown in FIG. 12 multiple skin grafts can be simultaneously produced by distributing aliquots of fibroblasts mixed with collagen hydrogel and of keratinocytes to multiple tissue forming chambers.

It should be noted that the specific time required for the cultivation of fibroblasts in the hydrogel before keratinocytes are seeded, and the time required for the cultivation of both fibroblasts and keratinocytes after the addition of keratinocytes and until the tissue is ready for grafting is dependent on the initial concentrations of cells seeded in the tissue formation device.

As will be apparent to the skilled person, a variety of robotic elements can be provided along the process, for the handling of samples and sample products at various stages.

Furthermore, suitable software can easily be devised by the skilled person and is not discussed herein in detail, for the sake of brevity. Thus the entire process of skin graft production may be situated in a closed system, the components of which (i.e., modules, devices, apparatuses and/or chambers) are operated and controlled in an automated manner, namely, the process of producing a skin graft is subject to coordinated control by a control module. The transfer of biological material, such as biopsy, skin pieces, skin layers and cells between the components may be also automatically controlled, as well as the management of fluids, waste and disposables.

According to one embodiment of the invention, a closed automated system is provided, such that biological material (other than waste products and samples used for offline quality control or biobanking) may not exit the system from the time the biopsy is received in the system and until the graft is ready for transplantation. This can be achieved in a fully-automated system by providing a regulated channel of fluid communication between the devices/apparatuses of the system. In a semi-automated system, the end product of each apparatus/module can be collected, for example in a retention bag, sealed, removed from said apparatus/module and (manually) connected to another apparatus/module, and all the while maintained under sterile conditions. It should be noted that both the fully-automated system and the semi-automated system are encompassed by the present invention and termed herein simply as "automated system". Similarly, the term "automated production" refers to both a fully-automated production and a semi-automated production.

Carrying out production of bio-engineered tissue may require the use of disposables (sometimes referred to as "consumables"), namely, a supply of equipment for one time use for handling biological materials, including tubes, containers, pipetting tips, and essentially any equipment that comes into direct contact with a biological material (including media and other solutions) that should be kept sterile in order to avoid contamination of the system. Of course, in an automated system, the management of the disposables (such as discarding used disposables and providing new disposables) is automatically controlled.

In addition, monitoring devices, such as cameras and various sensors (such as for pH temperature, humidity, etc.) can be deployed throughout the process.

In one embodiment of the invention, the biopsy received by the cell preparation device is a split-thickness biopsy containing the epidermis layer and a portion of the underlying dermis layer of the skin, having a thickness ranging from 200 µm to 600 µm. In another embodiment of the invention, the biopsy received by the cell preparation device is a full-thickness biopsy, namely, a biopsy containing the epidermis layer and the entire dermis layer (until the hypodermis layer is reached), having a thickness of between 600 and 1000 µm. The thickness of the biopsy may be dependent on the location of the harvest site.

The maximum area of the biopsy is largely dependent on the surgeon's/physician's evaluation of the damage caused to the patient due to the harvesting of the biopsy. The area of the biopsy is also dependent on the size of the tissue that is required for grafting. If no limitation of time is set, the cells can be repeatedly proliferated in the cell expansion device, such that the method of invention provides a continuous supply of isolated cells from which skin grafts can be formed, and as long as the cells maintain their viability at later passages. In one embodiment of the invention, the ratio of the harvest size to treatment size is 1:1 to 1:1000, specifically 1:9 to 1:500, more specifically 1:9 to 1:350, even more specifically 1:100 to 1:350. In a non-limiting example, the biopsy has an area of at least 0.1 cm². In another non-limiting example, 0.5 m² of tissue can be produced by the method of the invention from a biopsy having an area of 15-20 cm². In yet another non-limiting example, a skin graft having an area of about 0.11 m² can be produced by the method of the invention from a biopsy having an area of about 12 cm² within about 10-16 days.

The tissue produced by the method described herein is typically a full-thickness skin graft (FTSG), containing an epidermis layer and the entire dermis layer and characterized by a thickness of 600-1000 µm. Production of a split-thickness skin graft (STSG), containing an epidermis layer and a portion of a dermis layer and characterized by a thickness of 200-600 µm, is also encompassed by the present invention. The thickness of the skin graft produced by the method of the invention can be adjusted, in one embodiment of the invention, by the level of compression of the hydrogel, such that less compression results in a thicker skin graft.

In a further embodiment of the invention, living skin tissue at an area of 2 m² or less (for example, 1.5-2 m² or less) can be produced by the method of the invention, thus providing a possible treatment area that is 100% of the skin surface area of an average adult human. In a specific embodiment of the invention, skin graft having an area of about 0.5 m² is produced by the method described herein, which is roughly a quarter of the skin surface area of an average adult human. Importantly, this value is currently considered as the largest area of skin that can be transplanted in a single grafting procedure.

Although embodiments of the invention have been described by way of illustration, it will be understood that the invention may be carried out with many variations, modifications, and adaptations, without exceeding the scope of the claims.

The invention claimed is:

1. A method for producing a skin graft, comprising:
connecting a biopsy kit containing a skin biopsy sample to a layer separation chamber;
enzymatically separating the skin biopsy into a dense dermis layer and a less dense epidermis layer in said layer separation chamber, and transferring the dense dermis layer by flushing through a first outlet, and transferring the less dense epidermis layer by flushing through a second outlet, the separation chamber being assisted by external agitation;
isolating single cell suspension of fibroblasts and keratinocytes from the separated dermis and epidermis layers of the biopsy sample respectively, and transferring the isolated fibroblasts to one chamber and the isolated keratinocytes to a second chamber;

expanding fibroblasts and keratinocytes in their respective first and second chambers, and transferring the expanded fibroblasts and keratinocytes to first and second reservoirs respectively;
processing the fibroblasts and keratinocytes in their respective reservoirs; and
forming a skin graft comprising fibroblasts and keratinocytes from the processed fibroblasts and keratinocytes;
wherein connecting, separating, isolating, expanding, processing, and forming are subject to the automation of the process.

2. The method according to claim 1, wherein the transferring of the dermis layer, epidermis, layer, isolated fibroblasts and keratinocytes, expanded fibroblasts and keratinocytes, and processed fibroblasts and keratinocytes is subject to automatic control.

3. The method according to claim 1, further comprising adding at least one of melanocytes, endothelial cells and skin mesenchymal-derived cells to said processed fibroblasts or processed keratinocytes.

4. The method of claim 1, wherein the ratio between the size of the biopsy and the size of the skin graft is 1:9 to 1:1000.

5. The method according to claim 4, wherein the skin biopsy is a split-thickness biopsy and the skin graft is a full-thickness skin graft.

6. The method of claim 2, further comprising adding at least one of melanocytes, endothelial cells and skin mesenchymal-derived cells to said processed fibroblasts or processed keratinocytes.

7. The method of claim 2, wherein the ratio between the size of the biopsy size and the size of the skin graft is 1:9 to 1:1000.

8. The method of claim 3, wherein the ratio between the size of the biopsy size and the size of the skin graft is 1:9 to 1:1000.

9. A method comprising:
enzymatically separating a skin biopsy into a dense dermis layer and a less dense epidermis layer in a chamber at least partially filled with liquid;
separating the dense dermis layer from the less dense epidermis layer by flushing the dermis layer through a first outlet and flushing the epidermis layer through a second outlet situated above said first outlet with the assistance of external agitation;
isolating a single cell suspension of fibroblasts from the dermis layer and a single cell suspension of keratinocytes from the epidermis layer, and
transferring the isolated fibroblasts to one chamber and the isolated keratinocytes to a second chamber.

* * * * *